(12) United States Patent
Harvis

(10) Patent No.: US 10,245,177 B2
(45) Date of Patent: Apr. 2, 2019

(54) TEMPERATURE CONTROLLED BLANKET

(71) Applicant: Eva Harvis, Mt. Opton, NY (US)

(72) Inventor: Eva Harvis, Mt. Opton, NY (US)

( * ) Notice: Subject to any disclaimer, the term of this patent is extended or adjusted under 35 U.S.C. 154(b) by 0 days.

(21) Appl. No.: 15/830,881

(22) Filed: Dec. 4, 2017

(65) Prior Publication Data

US 2018/0153738 A1 Jun. 7, 2018

Related U.S. Application Data

(60) Provisional application No. 62/429,408, filed on Dec. 2, 2016.

(51) Int. Cl.
| | |
|---|---|
| *H05B 1/02* | (2006.01) |
| *A61F 7/00* | (2006.01) |
| *H05B 3/34* | (2006.01) |
| *A61F 7/02* | (2006.01) |

(52) U.S. Cl.
CPC ............ *A61F 7/0097* (2013.01); *A61F 7/007* (2013.01); *H05B 3/342* (2013.01); *A61F 2007/0086* (2013.01); *A61F 2007/0295* (2013.01); *A61F 2007/0298* (2013.01)

(58) Field of Classification Search
CPC ....... A41D 1/005; A61F 7/0097; A61F 7/007; H05B 3/342; H05B 1/0272; H05B 3/023
USPC .......................... 219/212, 211, 497, 483, 489
See application file for complete search history.

(56) References Cited

U.S. PATENT DOCUMENTS

| | | | | |
|---|---|---|---|---|
| 3,508,284 | A | | 4/1970 | Marquette |
| 3,634,655 | A | * | 1/1972 | Jordan .................... H05B 3/342 174/69 |
| 3,739,142 | A | * | 6/1973 | Johns ...................... H05B 3/342 219/212 |
| 4,132,262 | A | * | 1/1979 | Wibell .................. A47G 9/0215 165/206 |
| 4,162,393 | A | * | 7/1979 | Balboni ............... A47C 21/048 219/217 |
| 5,105,067 | A | * | 4/1992 | Brekkestran ....... G05D 23/2401 2/69 |
| 6,643,872 | B1 | | 11/2003 | Buswell |
| 6,686,561 | B2 | * | 2/2004 | Horey ................. A41D 31/0033 165/240 |
| 6,862,760 | B2 | | 3/2005 | Bradley et al. |
| 7,200,883 | B2 | | 4/2007 | Haggerty |

(Continued)

*Primary Examiner* — Mark Paschall
(74) *Attorney, Agent, or Firm* — Global Intellectual Property Agency, LLC; Daniel Boudwin

(57) ABSTRACT

A temperature controlled blanket for providing dual warming and cooling zones. The temperature controlled blanket comprises a first layer of material, a second layer of material, and a seam, wherein the seam is disposed along a longitudinal axis of each layer of material, such that the seam defines a first portion and a second portion of the blanket. The first portion and the second portion each contain a panel comprising heating and cooling elements disposed between the first layer of material and second layer of material. The blanket further comprises at least one thermostat operably connected to each panel of the first portion and the second portion and a power source, wherein the at least one thermostat individually controls the heating and cooling elements of each panel. In an alternative embodiment, the first portion and the second portion of the second layer of material are made of two differing fabrics.

11 Claims, 3 Drawing Sheets

(56) References Cited

U.S. PATENT DOCUMENTS

| | | | |
|---|---|---|---|
| 7,566,846 B1* | 7/2009 | Sorensen | H05B 1/02 |
| | | | 2/905 |
| 9,149,137 B2 | 10/2015 | Liddick | |
| 2009/0289046 A1* | 11/2009 | Richmond | A41D 13/0051 |
| | | | 219/211 |

* cited by examiner

TEMPERATURE CONTROLLED BLANKET

CROSS REFERENCE TO RELATED APPLICATION

This application claims the benefit of U.S. Provisional Application No. 62/429,408 filed on Dec. 2, 2016. The above identified patent application is herein incorporated by reference in its entirety to provide continuity of disclosure.

BACKGROUND OF THE INVENTION

The present invention relates to temperature controlled blankets, such as, heating blankets. More specifically, the present invention provides a temperature controlled blanket having heating and cooling capabilities in separate portions of the blanket that individually provide a preferred temperature to a user. The temperature controlled blanket allows sleeping partners to individually control a respective portion of the blanket to match their preferred temperature, while further providing the comfort and security of using a blanket. Furthermore, each portion of the blanket is made up of varying fabrics, such as, cotton and fleece, to match a comfort preference of the user. In an alternative embodiment, the temperature controlled blanket may be configured as a sheet that is placed over a mattress, wherein the user sleeps thereon.

Sleeping partners may prefer different sleeping temperatures and blanket preferences. Sheets or blankets might be thrown onto the floor or kicked to the bottom of a bed if one partner is warm during the night. However, this may leave the other partner feeling cold and upset as blankets are pulled or removed from the bed. With sleeping partners preferring different temperatures at night, finding a compromise might be difficult. Partners may begin sleeping in separate beds or in other bedrooms to obtain a good night's rest. Furthermore, many sleeping partners may have an affinity for different blanket fabrics. One partner may desire a lighter fabric, such as, cotton for their blanket. While another partner may prefer a warmer material, such as, fleece. Therefore, there is a need for a blanket having two halves being constructed of different fabrics, wherein each half includes heating and cooling elements that are independently controllable by a thermostat.

Devices have been disclosed in the known art that relate to temperature controlled blankets. These include devices that have been patented and published in patent application publications. These devices generally relate to heating blankets that are operably controlled by a thermostat and further contain varying layers of fabric. Some devices include dual fabric sheets or bedding for a bed. While other devices include dual fabric blankets having varying layers and portions of fabric.

These known art devices have several known drawbacks. While many of the temperature controlled blankets contain thermostats to regulate the heating element of the blanket, none of these blankets include a cooling means. Further, many of these temperature controlled blankets do not include two different portions of fabric, wherein each portion is configured to a preference of a user, such as, fleece and cotton. Finally, many of these blankets only contain a thermostat capable of controlling the temperature of the entire blanket, and not individual portions.

In light of the devices disclosed in the known art, it is submitted that the present invention substantially diverges in design elements from the known art and consequently it is clear that there is a need in the art for an improvement to existing temperature controlled blanket devices. In this regard, the instant invention substantially fulfills these needs.

SUMMARY OF THE INVENTION

In view of the foregoing disadvantages inherent in the known types of heating blankets now present in the known art, the present invention provides a new temperature controlled blanket wherein the same can be utilized for providing convenience for the user when individually controlling the heating and cooling temperature of dual portions of a blanket.

It is therefore an object of the present invention to provide a new and improved temperature controlled blanket that has all of the advantages of the known art and none of the disadvantages.

It is another object of the present invention to provide a temperature controlled blanket comprising a first layer of material, a second layer of material, and a seam, wherein the seam is disposed along a longitudinal axis of each layer of material, such that the seam defines a first portion and a second portion of the blanket. The first and second portion each further contain a panel comprising heating and cooling elements disposed between the first and second layer. The panels further comprise at least one thermostat operably connect to each panel of the first and second portion and a power source, wherein the at least one thermostat individually controls the heating and cooling elements of a first panel and the heating and cooling elements of a second panel.

Another object of the present invention is to provide a temperature controlled blanket wherein the first layer of material of the first and second portion is a first fabric, the second layer of material of the first portion is a second fabric, and the second layer of material of the second portion is a third fabric.

Yet another object of the present invention is to provide a temperature controlled blanket wherein the at least one thermostat is a digital thermostat.

Another object of the present invention is to provide a temperature controlled blanket that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
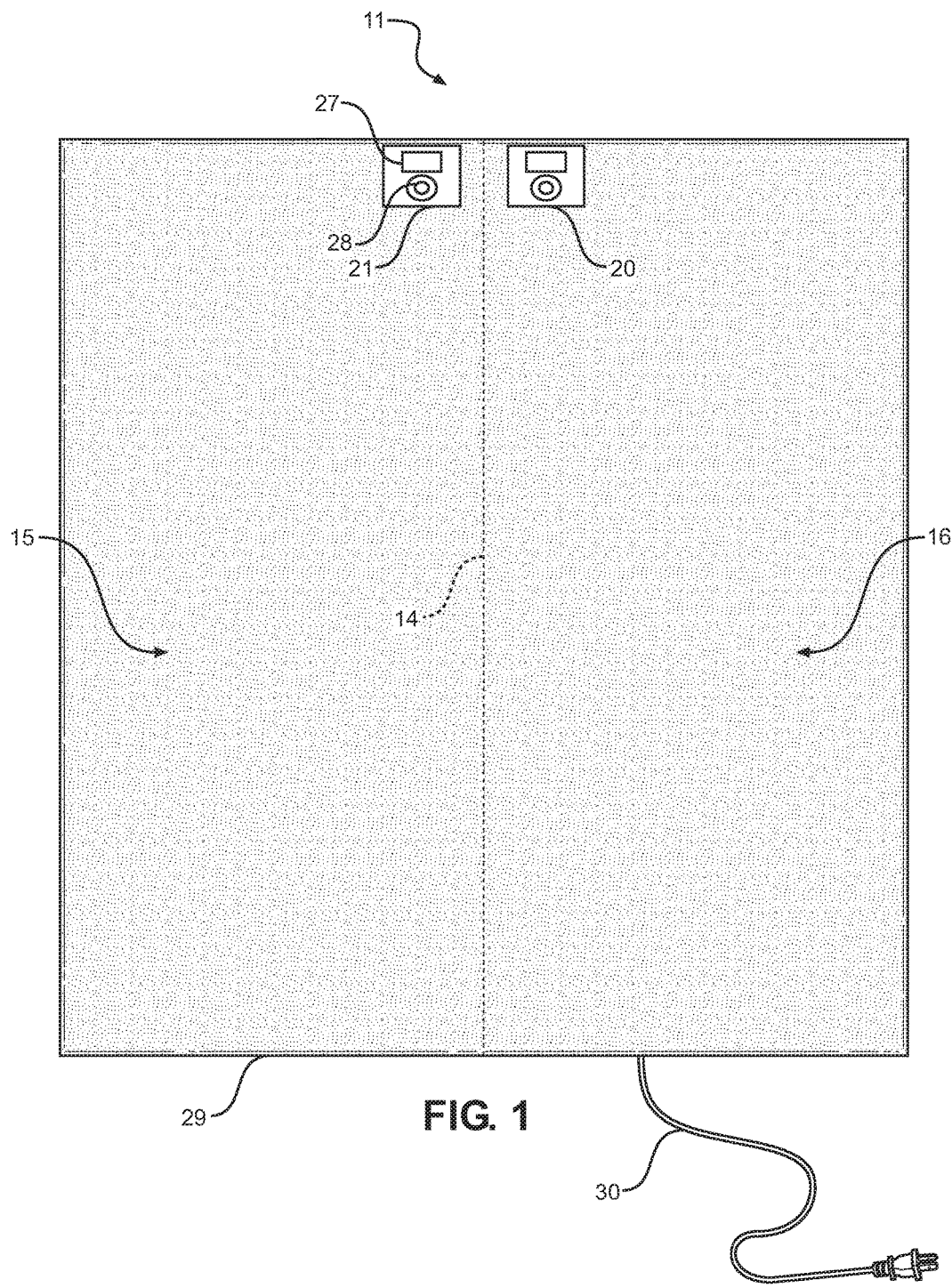
FIG. 1 shows an overhead view of an embodiment of the temperature controlled blanket.

Reference is made herein to the attached drawings. Like reference numerals are used throughout the drawings to depict like or similar elements of the temperature controlled blanket. For the purposes of presenting a brief and clear description of the present invention, the preferred embodiment will be discussed as used for covering a first user and a second user while in bed, wherein each user can individually control the heating and cooling temperature of the user's respective portion of the blanket. The figures are intended for representative purposes only and should not be considered to be limiting in any respect.

Figure 2:
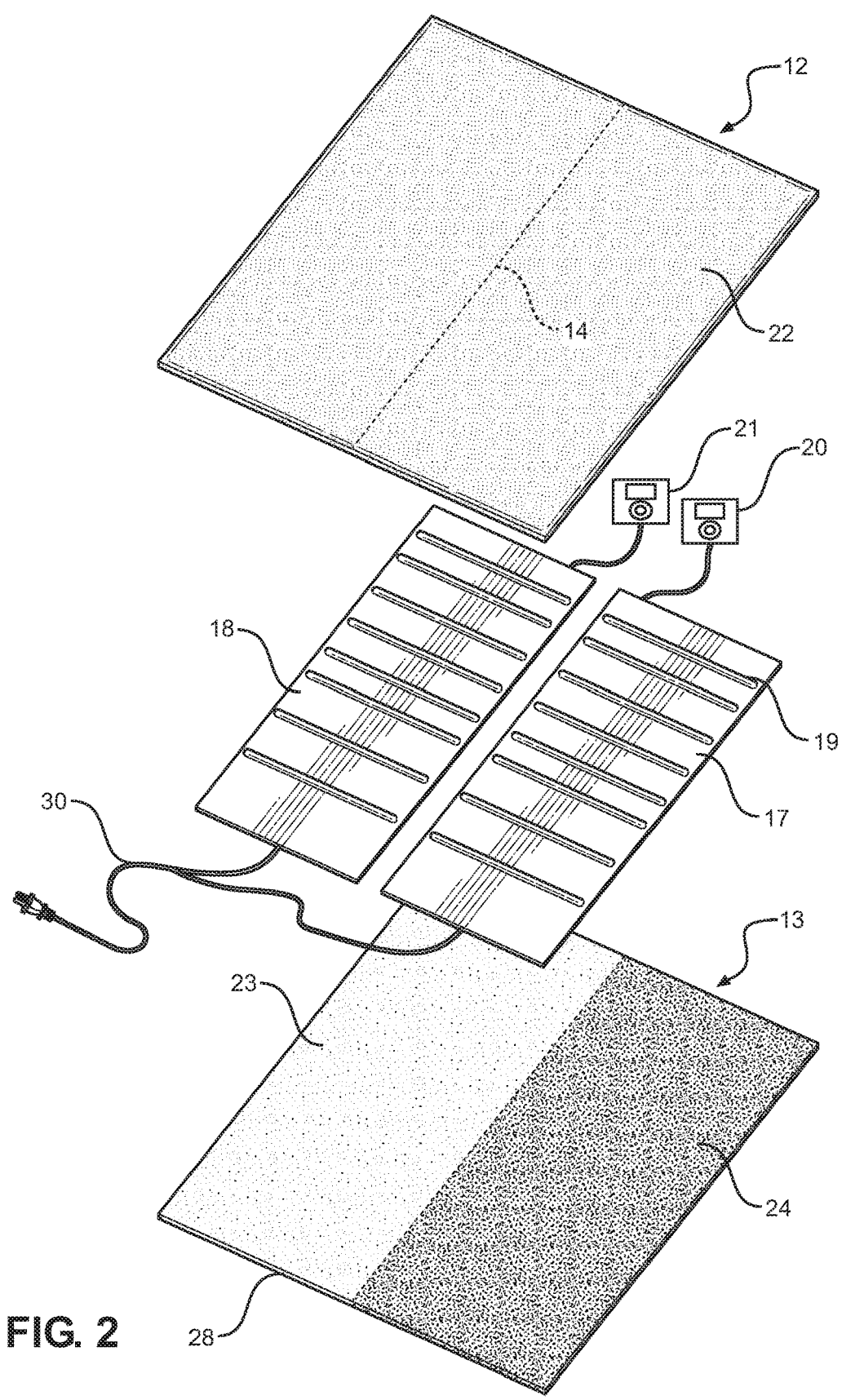
FIG. 2 shows an exploded view of an embodiment of the temperature controlled blanket.

Referring now to FIG. 1 and FIG. 2, there is shown an overhead view of an embodiment of the temperature controlled blanket and an exploded view of an embodiment of the temperature controlled blanket, respectively. The temperature controlled blanket 11 comprises a first layer of material 12 and a second layer of material 13, wherein the first layer of material 12 and the second layer of material 13 are affixed to each other at the outer perimeter 29 of each layer creating an enclosed interior volume. The temperature controlled blanket 11 further comprises a seam 14, wherein the seam 14 is disposed along a longitudinal axis of the first layer of material 12 and the second layer of material 13 such that the seam 14 defines a first portion 15 and a second portion 16 of the temperature controlled blanket 11. The seam 14 is disposed such that both the first portion 15 and the second portion 16 are equal in size and shape. In the illustrated embodiment, the temperature controlled blanket 11 comprises a rectangular shape, wherein each portion 15, 16 is configured to cover a first user and second user while sleeping in a bed. In alternative embodiments, the temperature controlled blanket 11 may comprise any suitable shape, such as, square, circle, or oval. In an alternative embodiment, the temperature controlled blanket 11, may be configured as a sheet, that is utilized to cover a mattress. In such an embodiment, the outer perimeter 29 of the first and second layer of material may further comprise an elastic band, configured to secure the layers to the mattress, such that it may be slept on by a user.

In the illustrated embodiment, the first portion 15 and second portion 16 of the blanket 11 each contain a panel 17, 18 comprising heating and cooling elements 19 disposed within the enclosed interior volume between the first layer of material 12 and the second layer of material 13. Each panel 17, 18 is operably connected to at least one thermostat 20, 21. In the illustrated embodiment, the temperature controlled blanket 11 includes a pair of thermostats 20, 21, wherein a first thermostat 20 individually controls the heating and cooling elements 19 of a first panel 17 and a second thermostat 21 individually controls the heating and cooling elements 19 of a second panel 18. However, in alternative embodiments, each panel may be individually controlled by a single thermostat. Both panels 17, 18 are operably connected to a power source 30. In the illustrated embodiment, the power source 30 is configured as an electrical cord that powers both panels 17, 18 and plugs into a standard electrical outlet. However, in alternative embodiments, a portable power source, such a battery, may be used.

In the illustrated embodiment, each thermostat 21, 20 is a digital thermostat. The digital thermostat includes a digital screen 27 and a knob 28 that adjusts a temperature reading on the digital screen 27. The thermostats 20, 21 are configured to adjust the operably connected panels 18, 19 according to the preference of a user, such that if a user is too warm, the user can lower the temperature reading on the thermostat 20, 21 to actuate the cooling element 19 to cool the panel 17, 18, in turn, cooling the first layer 12 and the second layer 13 of the blanket 11 within the corresponding portion 15, 16. Similarly, if a user is cold, the temperature reading on the thermostat 20, 21 can be increased to actuate the heating element 19 of the panel 17, 18, whereby the first layer 12 and the second layers 13 of the blanket 11 of the corresponding portion can be heated. The pair of thermostats 20, 21 allow a first user and a second user to individually control the temperature of the respective portion of the blanket 11. In this way, a user who prefers a cooler temperature, but desires the comfort and security of a blanket, can lower the temperature reading of their respective portion of the blanket to remain comfortable. This further prevents the user from removing the blanket from the bed and disrupting a second user from sleeping. While the second user, who prefers a warmer temperature when sleeping, can set their portion of the blanket to their preferred temperature, thus keeping both users comfortable.

In the illustrated embodiment, the first layer of material 12 further comprises a first fabric 22 in both the first and second portions 15, 16, while the second layer of material 13 comprises two different fabrics 23, 24, such that the second layer of material 13 of the first portion 15 is a second fabric 23, and the second layer of material 13 of the second portion 16 is a third fabric 24. In the illustrated embodiment, the first fabric 22 is cotton, the second fabric 23 is also cotton, and the third fabric 24 is fleece. In this way, the first layer of material 12 is a uniform fabric 22 across both portions of the blanket. Thus, from an overhead view when the temperature controlled blanket 11 is on a bed, it looks like a normal blanket. While the second layer of material 13 comprises two different fabrics 23, 24. This allows the blanket to be customized to the fabric preference of the user. As shown, the second fabric 23 is cotton, which is a cooler material, and the third fabric 24 is fleece, which is a warmer material.

Figure 3:
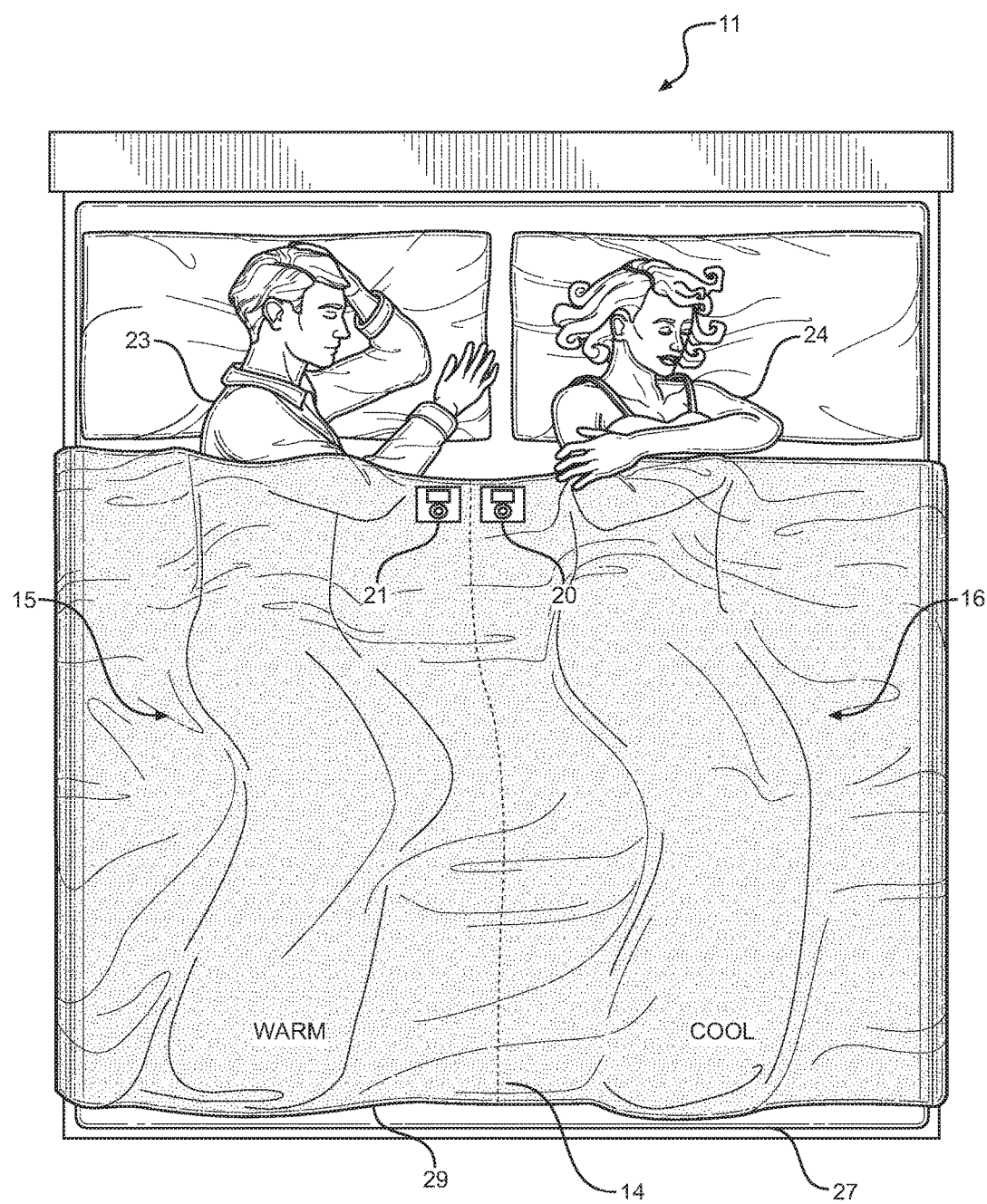
FIG. 3 shows an overhead view of an embodiment of the temperature controlled blanket in use.

Referring now to FIG. 3, there is shown an overhead view of an embodiment of the temperature controlled blanket in use. The temperature controlled blanket 11 is configured to cover a first user 23 and a second user 24 while sleeping in a bed. In the illustrated embodiment, the outer perimeter 29 of the blanket 11 is adapted to match a perimeter 27 of a double bed. However, in alternative embodiments, the outer perimeter 29 of the blanket 11 can be adapted to match any type of bed, such as, a king or queen bed. Each user 23, 24 can separately control a respective thermostat 21, 20, such that the first thermostat 20 controls the temperature of the first portion 16 of the blanket 11, and the second thermostat 21 controls the temperature of the second portion 15 of the blanket. Each portion 15, 16 of the blanket 11 remains separated by the seam 14 disposed down the longitudinal access. In the illustrated embodiment, the first user 23 has set the thermostat 21 to warm, wherein the heating elements of the first panel will continuously warm the respective portion 15 of the blanket to maintain a set temperature, while the second user 24 has the thermostat 20 set to a temperature necessitating cooling. This will cause the cooling element of the panel to continuously cool the respective portion 16 of the blanket to maintain a cooler temperature. The pair of thermostats 20, 21 and the separate portions 15, 16 of the blanket 11 allow each user 23, 24 to set a temperature according to their preference. The temperature controlled blanket 11 will keep users with different temperature preferences comfortable under the blanket while sleeping.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A temperature controlled blanket, comprising:
   a first layer of material and a second layer of material, wherein the first layer of material and the second layer of material are affixed to one another along an outer perimeter of each layer creating an enclosed interior volume;
   a seam, wherein the seam is disposed along a longitudinal axis of the first layer of material and the second layer of material, such that the seam defines a first portion and a second portion; wherein the first portion of the first layer of material and the first portion of the second layer of material are made of a first pair of fabrics; wherein the second portion of the first layer of material and second portion of the second layer of material are made of a second pair of fabrics; wherein the first pair of fabrics comprises at least one different fabric other than the second pair of fabrics;
   wherein the first portion and the second portion each contain a panel comprising heating and cooling elements disposed within the enclosed interior volume between the first layer of material and the second layer of material;
   at least one thermostat operably connected to each panel of the first portion and the second portion, wherein the at least one thermostat is configured to separately control the heating and cooling elements of each panel; and
   a power source, wherein the power source is operably connected to the first panel and the second panel.

2. The temperature controlled blanket of claim 1, wherein the first layer of material of the first portion and the second portion is a first fabric, the second layer of material of the first portion is a second fabric, and the second layer of material of the second portion is a third fabric.

3. The temperature controlled blanket of claim 2, wherein the first fabric is cotton, the second fabric is fleece, and the third fabric is cotton.

4. The temperature controlled blanket of claim 1, wherein the at least one thermostat is a digital thermostat.

5. The temperature controlled blanket of claim 4, wherein the digital thermostat contains a digital screen and a control knob.

6. The temperature controlled blanket of claim 1, wherein the first layer of material and the second layer of material comprise a rectangular shape.

7. The temperature controlled blanket of claim 1, wherein the outer perimeter is configured to match a perimeter of a bed.

8. The temperature controlled blanket of claim 1, wherein each the first portion and the second portion are configured to cover a user.

9. The temperature controlled blanket of claim 1, wherein the power source is an electrical cord.

10. The temperature controlled blanket of claim 1, wherein the at least one thermostat comprises a pair of thermostats operably connected to each panel of the first portion and the second portion, wherein a first thermostat individually controls the heating and cooling elements of a first panel and a second thermostat individually controls the heating and cooling elements of a second panel.

11. The temperature controlled blanket of claim 1, wherein the first portion and the second portion are equal in size and shape.

* * * * *